United States Patent
Fitch et al.

(10) Patent No.: US 9,018,227 B2
(45) Date of Patent: Apr. 28, 2015

(54) NICOTINIC ACETYLCHOLINE RECEPTOR AGONISTS

(75) Inventors: Richard W. Fitch, Terre Haute, IN (US); Thomas F. Spande, Bethesda, MD (US); H. Martin Garraffo, North Bethesda, MD (US); Herman J. C. Yeh, Potomac, MD (US); John W. Daly, Portland, OR (US); Kathryn Daly, legal representative, Portland, OR (US)

(73) Assignees: Indiana State University, Terre Haute, IN (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 262 days.

(21) Appl. No.: 13/583,420

(22) PCT Filed: Mar. 18, 2011

(86) PCT No.: PCT/US2011/028989
§ 371 (c)(1),
(2), (4) Date: Apr. 16, 2013

(87) PCT Pub. No.: WO2011/116282
PCT Pub. Date: Sep. 22, 2011

(65) Prior Publication Data
US 2013/0281482 A1  Oct. 24, 2013

Related U.S. Application Data

(60) Provisional application No. 61/315,674, filed on Mar. 19, 2010.

(51) Int. Cl.
| | | |
|---|---|---|
| A01N 43/42 | (2006.01) |
| A61K 31/44 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| A61K 31/437 | (2006.01) |
| C07D 491/14 | (2006.01) |
| A01N 43/90 | (2006.01) |
| C07D 491/147 | (2006.01) |
| G01N 33/50 | (2006.01) |

(52) U.S. Cl.
CPC ............ *A61K 31/437* (2013.01); *C07D 491/14* (2013.01); *A01N 43/90* (2013.01); *C07D 491/147* (2013.01); *G01N 33/5005* (2013.01)

(58) Field of Classification Search
CPC ... A01N 43/90; A61K 31/437; C07D 491/14; C07D 491/147
USPC ............................................ 514/287; 546/64
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 2008/0058315 A1 | 3/2008 | Cai et al. |
| 2009/0291921 A1 | 11/2009 | Jabri et al. |

OTHER PUBLICATIONS

Fitch et al. "Epiquinamide: A Poison That Wasn't From a Frog That Was1" J Nat Prod, Feb. 2009, vol. 72(2),pp. 243-247.*
Avalos et al., "Effects of Pyridine Ring Substitutions on Affinity, Efficacy, and Subtype Selectivity of Neuronal Nicotinic Receptor Agonist Epibatidine," *J. Pharmacol. Exp. Ther.*, 302 (3), 1246-1252 (2002).
Chase et al., "Enantioselective Synthesis of Aminocyclobutanol," (poster presentation at American Chemical Society National Meeting, Mar. 2008, New Orleans).
Ellis et al., "Synthetic Studies Toward Phantasmidine," (poster presentation, Indiana State University, Apr. 2006).
Fitch et al., "Acylcholine derivatives based on enantioenriched aminocyclanols," *237th ACS Meeting*, Salt Lake City, Mar. 22-26, 2009.
Fitch et al., "Bioassay-Guided Isolation of Epiquinamide, a Novel Quinolizidine Alkaloid and Nicotinic Agonist from an Ecuadoran Poison Frog, *Epipedobates tricolor*," *J. Nat. Prod.*, 66 (10), 1345-1350 (2003).
Fitch et al., "Membrane potential fluorescence: A rapid and highly sensitive assay for nicotinic receptor channel function," *Proc. Natl. Acad. Sci. USA*, 100 (8), 4909-4914 (2003).
Fitch et al., "Phantasmidine: A Novel Nicotinic Agonist from *Epipedobates anthonyi*," (poster presentation, American Chemical Society National Meeting, Mar. 2010 (San Francisco).
Fitch et al., "Phantasmidine: An Epibatidine Congener from the Ecuadorian Poison Frog *Epipedobates anthonyi*," *J. Nat. Prod.*, 73 (3), 331-337 (2010).

(Continued)

*Primary Examiner* — Kendra D Carter
(74) *Attorney, Agent, or Firm* — Leydig, Voit & Mayer, Ltd.

(57) ABSTRACT

The invention provides novel nicotinic acetylcholine receptor agonists, for example, phantasmidine and derivatives thereof, for example a compound of formula (I). Also disclosed are methods of treating disorders responsive to nicotinic acetylcholine receptor agonists such as Alzheimer's disease, schizophrenia, Myasthenia Gravis, Tourette's syndrome, Parkinson's disease, epilepsy, pain, and cognitive dysfunction by treatment with the nicotinic acetylcholine for agonists.

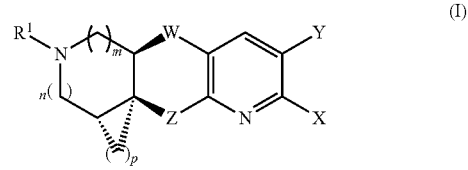

6 Claims, No Drawings

(56) References Cited

OTHER PUBLICATIONS

Fitch et al., Bioassay Guided Isolatin of New Nicotinic Agonists (Gordon Research Conference, Jul. 2003).

Jorenby et al., "Efficacy of Varenicline, an α4β2 Nicotinic Acetylcholine Receptor Partial Agonist, vs Placebo or Sustained-Release Bupropion for Smoking Cessation," *J. Am. Med. Assoc.*, 296 (1), 56-63 (2006).

Parker et al., "Neuronal Nicotinic Receptor β2 and β4 Subunits Confer Large Differences in Agonist Binding Affinity," *Mol. Pharmacol.*, 54, 1132-1139 (1998).

Salas et al., "Decreased Signs of Nicotine Withdrawal in Mice Null for the 4 Nicotinic Acetylcholine Receptor Subunit," *J. Neurosci.*, 24 (45), 10035-10039 (2004).

Shulte et al., "Synthetic Studies on 2,5-Dichlorohomonicotinic Acid," (poster presentation at Eli Lilly and Company, Aug. 2008).

Xiao et al., "The Comparative Pharmacology and Up-Regulation of Rat Neuronal Nicotinic Receptor Subtype Binding Sites Stably Expressed in Transfected Mammalian Cells," *J. Pharmacol. Exp. Ther.*, 310 (1), 98-107 (2004).

\* cited by examiner

NICOTINIC ACETYLCHOLINE RECEPTOR AGONISTS

CROSS REFERENCE TO RELATED APPLICATIONS

This patent application is the U.S. national phase of International Patent Application No. PCT/US2011/028989, filed Mar. 18, 2011, which claims the benefit of U.S. Provisional Patent Application No. 61/315,674, filed Mar. 19, 2010, the disclosure of which is incorporated by reference.

BACKGROUND OF THE INVENTION

Amphibians in general, and poison frogs in particular, have been a significant source of biologically active natural products.[1,2] A number of frog-skin alkaloids have been shown to have activity at nicotinic acetylcholine receptors.[3,4] The ability of poison frogs to sequester alkaloids from their diet results in a unique complexity and to date over 800 alkaloids in more than 20 structural classes have been characterized.

In 1992, epibatidine (1) was isolated and characterized from the frog *Epipedobates anthonyi* (formerly *Epipedobates tricolor*, Boulenger, 1899). This compound has become one of the most well-studied members of the frog alkaloids due to its potent analgesic activity resulting from activation of nicotinic receptors. However, the chemical complexity of this extract (over 80 alkaloids) has prompted the investigation of other alkaloids, including epiquinamide (2). Although the activity initially ascribed to this compound was later found to be due to a cross-contamination artifact, other compounds within this extract were also found to have nicotinic activity, such as the known N-methylepibatidine.

Nicotinic agonists, which enhance action at nicotinic acetylcholine receptors, have been shown to possess useful clinical activity in a number of diseases and disorders, such as in the treatment of dementia caused by Alzheimer's disease, treatment of tobacco dependence, treatment of glaucoma, and for use as short acting muscle relaxants. While certain nicotinic acetylcholine receptor agonists have been proposed, there remains an unmet need in the art for additional nicotinic acetylcholine receptor agonists.

BRIEF SUMMARY OF THE INVENTION

The invention provides Phantasmidine, particularly in isolated or purified form, or a pharmaceutically acceptable salt thereof.

The invention also provides a compound of Formula

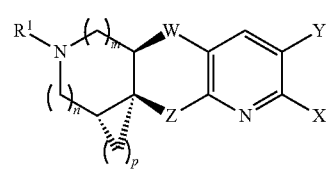

I

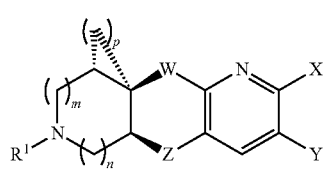

II

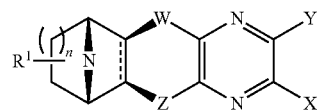

III

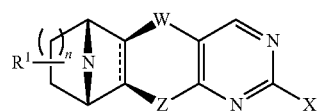

IV

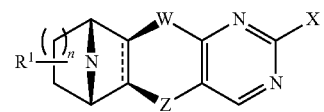

V

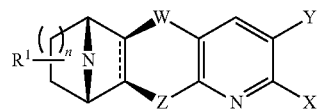

VI

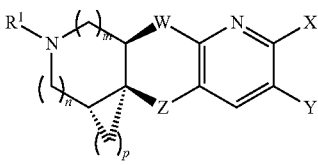

VII

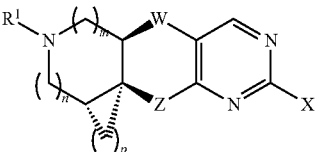

VIII

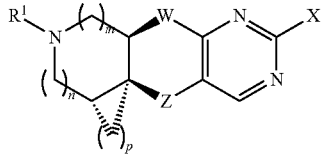

IX

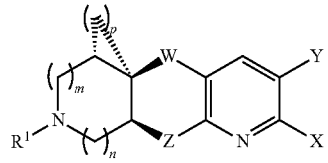

X

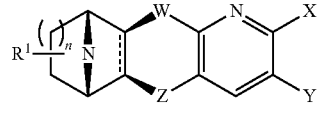

XI

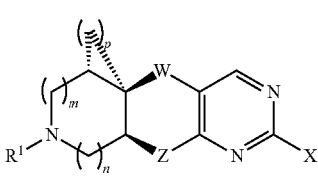

XII

-continued

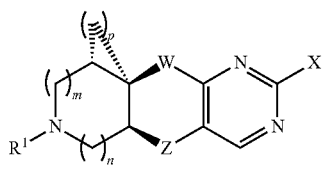

XIII wherein $R^1$ is selected from the group consisting of hydrogen, $C_1$-$C_{12}$ alkyl, $C_2$-$C_{12}$ alkenyl, $C_2$-$C_{12}$ alkynyl, $C_3$-$C_6$ cycloalkyl, $C_3$-$C_6$ cycloalkenyl, $C_7$-$C_{12}$ arylalkyl, $C_6$-$C_{10}$ aryl, heterocyclyl, heteroaryl, $R^2$CO, $R^2$OCO, and $R^2R^3$NCO, wherein $R^1$ other than hydrogen, is optionally substituted with one or more substituents selected from the group consisting of halogen, $C_1$-$C_6$ haloalkyl, $C_1$-$C_6$ dihaloalkyl, $C_1$-$C_6$ trihaloalkyl, —NO$_2$, —OH, —OR$^4$, —SH, —SR$^4$, —SOR$^4$, —SO$_2$R$^4$, —COR$^4$, —COOH, —COOR$^4$, —CONHR$^4$, and —CONR$^4$R$^5$, wherein W and Z are independently selected from the group consisting of CH$_2$, NR$^4$, NOR$^4$, O, S, SO, SO$_2$, or a bond, wherein X and Y are independently selected from the group consisting of hydrogen, aryl, heteroaryl, $C_1$-$C_{12}$ alkyl, $C_2$-$C_{12}$ alkenyl, $C_2$-$C_{12}$ alkynyl, OH, OR$^4$, SH, SR$^4$, SOR$^4$, SO$_2$R$^4$, COR$^4$, COOH, COOR$^4$, CONHR$^4$, CONR$^4$R$^5$, —C≡C(CH$_2$)$_q$NR$^4$R$^5$, and —C≡C(CH$_2$)$_q$SR$^4$, wherein $R^2$, $R^3$, $R^4$, and $R^5$ are independently selected from the group consisting of hydrogen, $C_1$-$C_{12}$ alkyl, $C_2$-$C_{12}$ alkenyl, $C_2$-$C_{12}$ alkynyl, $C_3$-$C_6$ cycloalkyl, $C_3$-$C_6$ cycloalkenyl, $C_7$-$C_{12}$ arylalkyl, $C_6$-$C_{10}$ aryl, heterocyclyl, heteroaryl, and wherein m and n are 0-3, p is 0-5, and q is 0-2, provided that the compound is not phantasmidine.

The invention further provides a pharmaceutical composition comprising the compound or salt of the invention and a pharmaceutically acceptable carrier.

The invention additionally provides a method for treating or preventing disorder responsive to a nicotinic acetylcholine receptor agonist, comprising administering to a mammal in need of treatment a therapeutically effective amount of a compound or salt of the invention.

The invention also provides a method of identifying a cell expressing a β4 nicotinic subunits, which method comprises (a) providing a cell, (b) exposing the cell to a membrane potential dye, (c) exposing the cell to a compound of the invention, and (d) determining the response of the cell to nicotine.

The invention also provides a use of the compound of any of the invention in the preparation of a medicament for treating or preventing disorder responsive to a nicotinic acetylcholine receptor agonist.

DETAILED DESCRIPTION OF THE INVENTION

In accordance with an embodiment, the invention provides a condensed tetracyclic alkaloid, which has been named Phantasmidine. Phantasmidine has been isolated and characterized from the frog *Epipedobates anthonyi* (formerly *Epipedobates tricolor*) and has been assigned the structure:

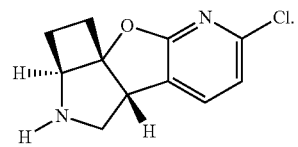

In a further embodiment, the invention provides compounds of Formulas I-XIII:

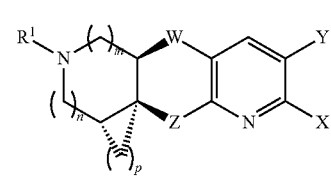

I

II

III

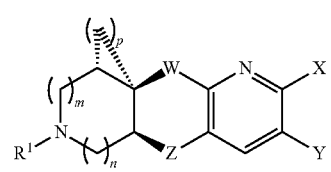

IV

V

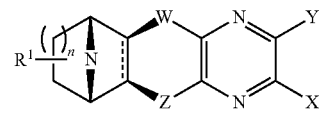

VI

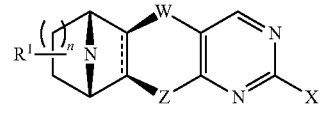

VII

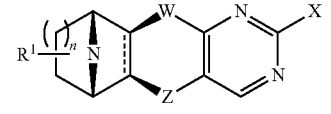

VIII

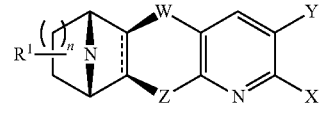

IX

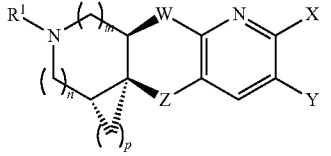

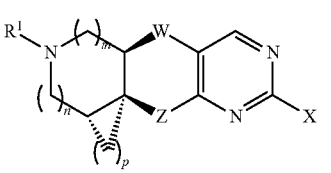

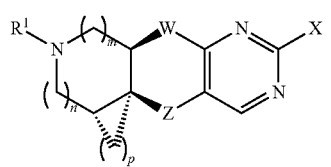

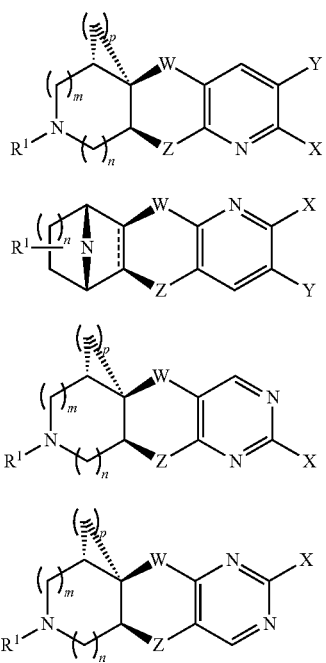

wherein $R^1$ is selected from the group consisting of hydrogen, $C_1$-$C_{12}$ alkyl, $C_2$-$C_{12}$ alkenyl, $C_2$-$C_{12}$ alkynyl, $C_3$-$C_6$ cycloalkyl, $C_3$-$C_6$ cycloalkenyl, $C_7$-$C_{12}$ arylalkyl, $C_6$-$C_{10}$ aryl, heterocyclyl, heteroaryl, $R^2CO$, $R^2OCO$, and $R^2R^3NCO$, wherein $R^1$ other than hydrogen, is optionally substituted with one or more substituents selected from the group consisting of halogen, $C_1$-$C_6$ haloalkyl, $C_1$-$C_6$ dihaloalkyl, $C_1$-$C_6$ trihaloalkyl, —$NO_2$, —OH, —SH, —$SR^4$, —SOW, —$SO_2R^4$, —$COR^4$, —COOH, —$COOR^4$, —$CONHR^4$, and —$CONR^4R^5$, wherein W and Z are independently selected from the group consisting of $CH_2$, $NR^4$, $NOR^4$, O, S, SO, $SO_2$, or a bond, wherein X and Y are independently selected from the group consisting of hydrogen, aryl, heteroaryl, $C_1$-$C_{12}$ alkyl, $C_2$-$C_{12}$ alkenyl, $C_2$-$C_{12}$ alkynyl, halogen, OH, $OR^4$, SH, $SR^4$, $SOR^4$, $SO_2R^4$, $COR^4$, COOH, $COOR^4$, $CONHR^4$, $CONR^4R^5$, —C≡C($CH_2$)$_q$$NR^4R^5$, and wherein $R^2$, $R^3$, $R^4$, and $R^5$ are independently selected from the group consisting of hydrogen, $C_1$-$C_{12}$ alkyl, $C_2$-$C_{12}$ alkenyl, $C_2$-$C_{12}$ alkynyl, $C_3$-$C_6$ cycloalkyl, $C_3$-$C_6$ cycloalkenyl, $C_7$-$C_{12}$ arylalkyl, $C_6$-$C_{10}$ aryl, heterocyclyl, heteroaryl, and wherein m and n are 0-3, p is 0-5, and q is 0-2, provided that the compound is not phantasmidine of the formula:

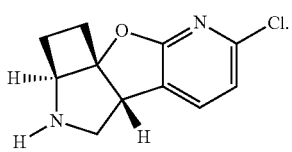 [SMILES: Clc1ccc2c(n1)O[C@@]13CC[C@@H]1NC[C@@H]23]

Referring now to terminology used generically herein, the term "alkyl" means a straight-chain or branched alkyl substituent containing from, for example, 1 to about 12 carbon atoms, preferably from 1 to about 8 carbon atoms, more preferably from 1 to 6 carbon atoms. Examples of such substituents include methyl, ethyl, propyl, isopropyl, n-butyl, sec-butyl, isobutyl, tert-butyl, pentyl, isoamyl, hexyl, heptyl, octyl, nonyl, decyl, undecyl, dodecyl, and the like.

The term "alkylene," as used herein, means a straight-chain or branched alkyl substituent containing from, for example, 2 to about 12 carbon atoms, preferably from 2 to about 6 carbon atoms, and is connected to two or more substituents at two or more different positions on the alkylene group.

The term "alkenyl," as used herein, means a linear alkenyl substituent containing at least one carbon-carbon double bond and from, for example, about 2 to about 12 carbon atoms (branched alkenyls are about 3 to about 12 carbons atoms), preferably from about 2 to about 8 carbon atoms (branched alkenyls are preferably from about 3 to about 8 carbon atoms), more preferably from about 2 to about 6 carbon atoms. Examples of such substituents include vinyl, propenyl, isopropenyl, n-butenyl, sec-butenyl, isobutenyl, tert-butenyl, pentenyl, isopentenyl, hexenyl, heptenyl, octenyl, nonenyl, decenyl, undecenyl, dodecenyl, and the like.

The term "alkenylene," as used herein, means a straight-chain or branched alkenyl substituent containing from, for example, 2 to about 12 carbon atoms, preferably from 2 to about 6 carbon atoms, and is connected to two or more substituents at two or more different positions on the alkenylene group.

The term "alkynyl," as used herein, means a linear alkynyl substituent containing at least one carbon-carbon triple bond and from, for example, 2 to about 12 carbon atoms (branched alkynyls are about 3 to about 12 carbons atoms), preferably from 2 to about 8 carbon atoms (branched alkynyls are preferably from about 3 to about 8 carbon atoms), more preferably from about 2 to about 6 carbon atoms. Examples of such substituents include ethynyl, propynyl, isopropynyl, n-butynyl, sec-butynyl, isobutynyl, tert-butyryl, pentynyl, isopentynyl, hexynyl, and the like.

The term "alkynylene," as used herein, means a straight-chain or branched alkynyl substituent containing from, for example, 2 to about 12 carbon atoms, preferably from 2 to about 6 carbon atoms, and is connected to two or more substituents at two or more different positions on the alkynylene group.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Preferably, the heterocyclyl group is an aromatic heterocyclyl group. Non-limiting examples of suitable heterocyclyl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl group is optionally substituted with 1, 2, 3, 4, or 5 substituents as recited herein, wherein the optional substituent can be present at any open position on the heterocyclyl group.

Whenever a range of the number of atoms in a structure is indicated (e.g., a $C_1$-$C_{12}$, $C_1$-$C_8$, $C_1$-$C_6$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), 2-12 carbon atoms (e.g., $C_2$-$C_{12}$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2$ π electrons, according to Hückel's Rule.

The term "arylene" refers to an unsubstituted or substituted aromatic carbocyclic substituent as defined herein, wherein the arylene substituent is connected to two or more substituents at two or more different positions on the arylene group. For example, 1,2-dichlorobenzene can be considered to be a phenylene (arylene) group substituted with two chlorine atoms.

The term "heteroaryl" refers to an unsubstituted or substituted aromatic heterocyclic substituent, as commonly understood in the art. It is understood that the term heteroaryl applies to cyclic heterocyclic substituents that are planar and comprise $4n+2$ π electrons, according to Hückel's Rule.

The invention contemplates embodiments in which a compound having one or more chiral centers is a substantially pure enantiomer thereof, a racemic mixture thereof, or a mixture containing any proportion of the two enantiomers thereof.

In accordance with certain embodiments, the compound has Formula I. In accordance with certain embodiments, the compound has Formula II.

In accordance with certain embodiments, m is 1, n is 0, p is 2, W is a bond, and Z is O.

In accordance with certain embodiments, $R^1$ is selected from the group consisting of hydrogen, $C_1$-$C_{12}$ alkyl, $C_2$-$C_{12}$ alkenyl, $C_2$-$C_{12}$ alkynyl, $C_3$-$C_6$ cycloalkyl, $C_3$-$C_6$ cycloalkenyl, $C_7$-$C_{12}$ arylalkyl, $C_6$-$C_{10}$ aryl, heterocyclyl, heteroaryl, and $R^2CO$.

In accordance with certain preferred embodiments, $R^1$ is selected from the group consisting of hydrogen, $C_1$-$C_{12}$ alkyl, $C_2$-$C_{12}$ alkenyl, $C_2$-$C_{12}$ alkynyl, and $R^2CO$.

In accordance with certain preferred embodiments, $R^1$ is hydrogen or $C_1$-$C_{12}$ alkyl.

In accordance with certain more preferred embodiments, $R^1$ is hydrogen or methyl.

In accordance with certain preferred embodiments, $R^1$ is $R^2CO$. In accordance with certain more preferred embodiments, $R^1$ is acetyl.

In accordance with certain preferred embodiments, X is chloro.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, e.g., intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

The present invention is additionally directed to a method for treating or preventing disorder responsive to a nicotinic acetylcholine receptor agonist, comprising administering to a mammal in need of treatment a therapeutically effective amount of a compound or salt of the invention. In certain embodiments the nicotinic acetylcholine receptors contain $\beta 4$ subunits. In certain preferred embodiments the nicotinic acetylcholine receptors contain $\alpha 4$ subunits and $\beta 4$ subunits. In certain preferred embodiments the nicotinic acetylcholine receptors contain $\alpha 4$ subunits and $\beta 4$ subunits and further contain $\alpha 7$ subunits.

In accordance with an embodiment, the invention provides a method of treating or preventing a disorder responsive to a nicotinic acetylcholine receptor agonist, comprising administering to a mammal in need of treatment a therapeutically effective amount of a compound or salt represented by Formulas I-XIII. The disorder can be any suitable disorder responsive to responsive to a nicotinic acetylcholine receptor agonist, for example, a disorder of the central nervous system. Examples of disorders of the central nervous system amenable to treatment with the inventive compounds include but are not limited to Alzheimer's disease, schizophrenia, Myasthenia Gravis, Tourette's syndrome, Parkinson's disease, epilepsy, and cognitive dysfunction.

In accordance with other embodiments, the invention provides a method of treating or preventing a disorder responsive to a nicotinic acetylcholine receptor agonist including tobacco dependence, glaucoma, cardiovascular disorders, pain, and the like. In accordance with an embodiment, the cardiovascular disorder is hypertension. In accordance with other embodiments, treatment of the disorder comprises relaxation of muscle tissue produced by treatment with the inventive compounds.

The term "mammal" includes, but is not limited to, the order Rodentia, such as mice, and the order Logomorpha, such as rabbits. It is preferred that the mammals are from the order Carnivora, including Felines (cats) and Canines (dogs).

It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

"Treating" within the context of the present invention, means an alleviation of symptoms associated with a disorder or disease, or halt of further progression or worsening of those symptoms, or prevention or prophylaxis of the disease or disorder. For example, within the context of treating patients with Alzheimer's disease, successful treatment may include an improvement in cognitive function as evaluated by tests well known in the art. Treatment may also include administering the pharmaceutical formulations of the present invention in combination with other therapies. The compounds of the invention can also be administered in conjunction with other nicotinic acetylcholine receptor agonists. Appropriate combinations can be determined by those of skill in the medical arts.

"Preventing" within the context of the present invention, refers to a prophylactic treatment of an individual prone or subject to development of a condition, in particular, a disease or disorder responsive to agonism of nicotinic acetylcholine receptors. For example, those of skill in the medical arts may be able to determine, based on clinical symptoms and patient history, a statistical predisposition of a particular individual to the development of the aforesaid disease or disorder. Accordingly, an individual predisposed to the development of a disease or disorder responsive to agonism of nicotinic acetylcholine receptors may be treated with a compound or a composition of the present invention in order to prevent, inhibit, or slow the development of the disease or disorder.

One skilled in the art will appreciate that suitable methods of utilizing a compound and administering it to a human for the treatment or prevention of disease states, in particular, Alzheimer's disease, schizophrenia, Myasthenia Gravis, Tourette's syndrome, Parkinson's disease, epilepsy, cognitive dysfunction, tobacco dependence, glaucoma, cardiovascular disorders such as hypertension, and the like which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the mammal.

The present invention is further directed to a method of identifying a cell expressing a β4 nicotinic subunit, which method comprises (a) providing a cell, (b) exposing the cell to a membrane potential dye, (c) exposing the cell to a compound of the invention, and (d) determining the response of the cell to nicotine. In certain embodiments, the compound is phantasmidine or the compound represented by Formula VI. In certain embodiments, the response of the cell to nicotine is determined by measurement of the fluorescence of the membrane potential dye.

The invention also provides a use of the compound of any of the invention in the preparation of a medicament for treating or preventing disorder responsive to a nicotinic acetylcholine receptor agonist. In certain embodiments, the disorder is selected from the group consisting of Alzheimer's disease, schizophrenia, Myasthenia Gravis, Tourette's syndrome, Parkinson's disease, epilepsy, and cognitive dysfunction. In certain other embodiments, the disorder is selected from the group consisting of tobacco dependence, glaucoma, cardiovascular disorders, and the like. In certain other embodiments, treatment of the disorder comprises relaxation of muscle tissue produced by treatment with the inventive compounds. The medicament typically is a pharmaceutical composition as described herein.

The invention additionally provides a method for killing insects comprising applying an insecticidal composition comprising an effective amount of a compound or salt a compound of the invention. The insect can be any insect selected from the phylum *Arthopoda*. One of ordinary skill in the art will readily comprehend a suitable insecticidal dosage of the inventive compound or salt thereof. The insecticidal composition can be any suitable insecticidal composition, many of which are well known in the art.

The compounds of the invention can be synthesized by any suitable method. For example, in an embodiment, compounds III-V and XI may be prepared by the following general scheme as illustrated below for compound VI, where n=1, W, Z=O, X=Cl, Y=H. Other members of this class may be prepared in similar manner by selection of the appropriately substituted pyridine, pyrimidine or pyrazine. The general considerations are as follows. The bicyclic ring may be installed by Diels-Alder reaction of an acylpyrrole with the appropriate pyridodioxin, with or without leaving group substitution on the dioxin ring. The pyridodioxin obtained from cyclization of a suitable glycolic acid equivalent and the appropriately substituted pyridine. These may be derived from commercially available glycolic acid and 2,6-dichloropyridine, respectively.

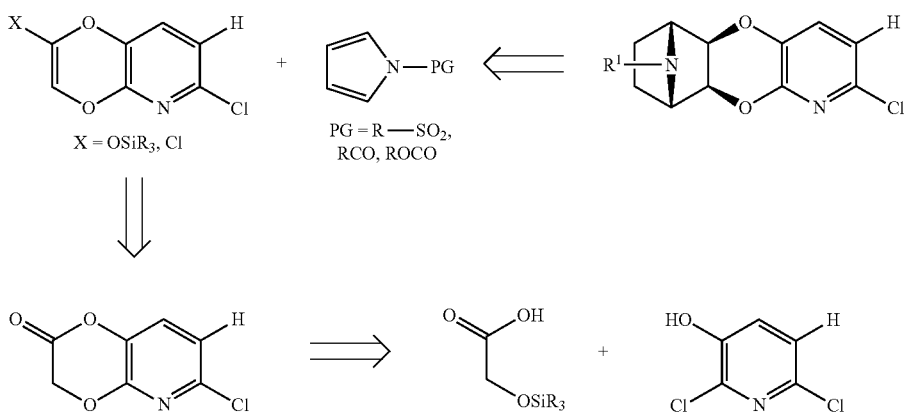

In another embodiment, compounds I, II, VII-X, XII, and XIII may be obtained through similar disconnections as illustrated for the case for compound X, where m, n, p=1, W=CH$_2$, Z=O, X=Cl, Y=H. The three membered ring may be installed using Simmons Smith methylenation with larger rings installed by photocycloaddition or Diels alder cycloaddition respectively. This intermediate is obtained by selective reduction of a pyridine ring via the acylpyridinium salt. This heterocycle is in turn available from cyclization of two substituted pyridines available from commercially available 4-methyl-3-pyridinol and 2,6-dichloropyridine, respectively.

determined by LC-UV-APCIMS. Also present but at substantially lower concentration were two chlorine-containing congeners of isotopic molecular weight 222/224. Each had significant bioactivity. However, this was incompletely resolved from that of the much more abundant epibatidine. The first alkaloid, eluting immediately prior to 1 was determined to be the known N-methylepibatidine (3) by LC-APCIMS and GC-EIMS and GC-CIMS comparison with authentic material.[6] Alkaloid 3 is essentially equipotent with epibatidine and its pharmacology has been described, though this is the first detection of 3 in Nature. Though isobaric with 3, the second

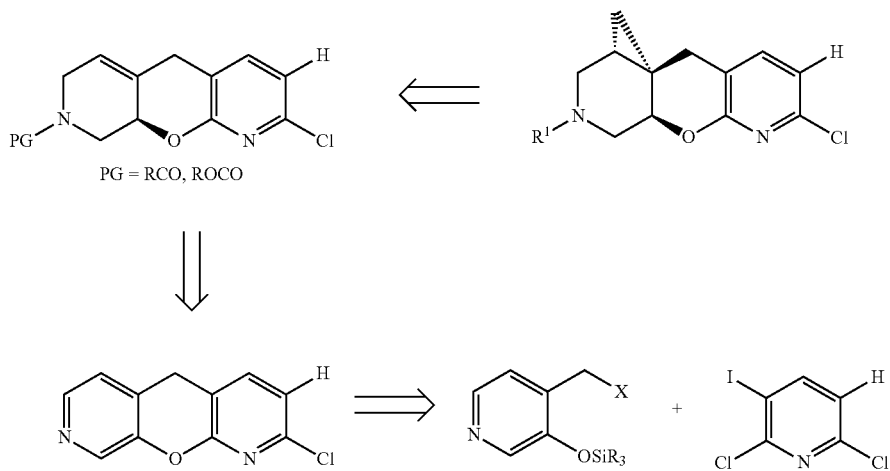

In an embodiment, the invention provides phantasmidine in isolated or purified form, or a pharmaceutically acceptable salt thereof.

The structure elucidation of phantasmidine was determined as follows. Collection, preparation of alkaloid fractions and preparative HPLC of *Epipedobates anthonyi* were performed as previously described.[9] In this extract over 80 alkaloids were found, including epibatidine (1). Bioassay analysis of isolated fractions in HEK cells expressing rat α3 and β4 nicotinic receptor subunits indicated at least three fractions having nicotinic-agonist activity. These included epiquinamide (2, with artifactual activity from cross contamination with epibatidine),[9,10] epibatidine (with the major activity of the three),[5] and a third active fraction eluting shortly after epibatidine. Epibatidine (1) was the major chlorinated compound present with molecular weight 208/210 as alkaloid (4) was determined to have an exchangeable hydrogen, and its EIMS was incompatible with such a simple epibatidine derivative as 3. Alkaloid 4 eluted shortly after 1 on LC-MS and its UV absorption at 260 nm suggested the presence of a pyridine ring, analogous to epibatidine.

Analytical and semi-preparative HPLC was conducted as described previously[9] with collection of fractions in 96-well plates and the wells sampled for assessment of nicotinic receptor activity in functional fluorescence assays in live cells using dyes sensitive to intracellular calcium levels or membrane potential (a surrogate for ionic flux).[11] Activity was assessed in several cell lines expressing various combinations of nicotinic-receptor subunits.[12-17] Comparison of the LC-MS trace with the time-bioactivity profile indicated 4 to be a nicotinic agonist. There were some initial concerns that cross-contamination by 1 might be responsible for the activity, based on previous experience in the isolation of 2.[10] However, the relative activity of 4 did not parallel 1 across several cell lines expressing different nicotinic-receptor subtypes (see below). This observation led to the conclusion that 4 is a novel alkaloid and nicotinic acetylcholine receptor agonist with altered subtype selectivity relative to 1. The structures of compounds 1-6 are set forth below.

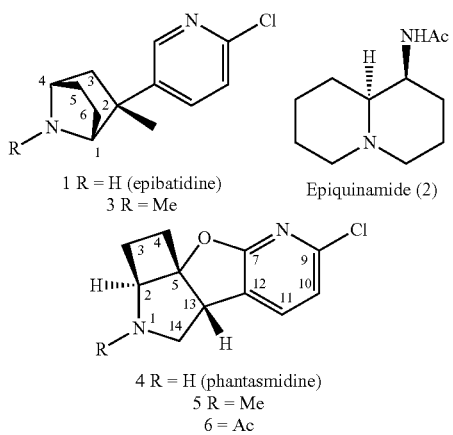

1 R = H (epibatidine)
3 R = Me

Epiquinamide (2)

4 R = H (phantasmidine)
5 R = Me
6 = Ac

The bulk of the initial characterization of 4 was performed by GC-MS and LC-APCI-MS during evaluation of the original extract. The GC-CIMS (NH$_3$) spectrum gave the expected [M+H]$^+$ ion at m/z 223/225 while deuterium-exchange using CI-ND$_3$ indicated a single exchangeable hydrogen. This was also observed with LC-APCI-MS when D$_2$O was used in place of H$_2$O in the mobile phase during the characterization of the initial extract. The GC-EIMS of 4 exhibited a molecular ion at m/z 222/224 and fragmentation that could generally be ascribed to α-cleavages of the three bonds adjacent to the pyrrolidine nitrogen.[18] There were two major complementary fragments at m/z 167/169 (M-C$_3$H$_5$N, base peak) and m/z 56 (C$_3$H$_6$N), and a third major peak at m/z 80. The latter peak appears to arise from facile ring expansion followed by a complex rearrangement and aromatization to afford a pyridinium ion derived from the pyrrolidine ring. Since the pyrrolidine N is lost as a neutral molecule to provide the base peak at m/z 167/169, the proposed fragmentation pathway requires another atom to carry the positive charge. This is possible using the oxygen atom, in which the radical ion is stabilized by the pyridine ring. Minor fragment pairs were also present at m/z 207/209 (M-CH$_3$) and m/z 194/196 (M-C$_2$H$_4$), the latter arising from cleavage of the cyclobutane ring with subsequent loss of ethylene. The rearrangement producing m/z 80 and the presence of a secondary amine were supported by co-injection of 4 with formalin-formic acid, effecting an Eschweiler-Clarke-type methylation in the 250° C. injector port to produce derivative 5.[19,20] The mass spectrum of 5 showed the expected shift of the molecular ion to m/z 236/238. Also noted were shifts of the m/z 56 and m/z 80 fragments in 4 to m/z 70 and m/z 94 respectively in 5, clearly indicating the aliphatic nitrogen to be present in each fragment as a secondary amine. A key observation was the absence of the m/z 167/169 base peak fragment of 4 with no mass-shifts equivalent in 5. EIMS of 4 in the presence of ND$_3$ produced shifts of +1 amu in each of the fragments, including m/z 167/169. These two observations suggested that the aliphatic NH of 4 is involved in the fragmentation producing m/z 167/169 in a way that the methyl group could not participate, involving the transfer of the amine H (or D when using ND$_3$).

Co-injection of 4 with acetic anhydride afforded in-situ formation of acetamide 6 with parent ion at m/z 264/266. This gave several fragments similar to 4, resulting from primary loss of the acetyl group as ketene to afford 4 directly. Thus, fragments at m/z 222/224, 167/169, 80, and 56 were observed in similar proportions as with 4, along with a fragment pair at m/z 221/223, which possibly gave rise to fragment pairs at m/z 193/195, and m/z 166/168.

Although HRFABMS was attempted on 4, only the $^{35}$Cl isotope peak for [M+H]$^+$ was identified unambiguously. However, a satisfactory HREIMS value for both isotopic parent ions was obtained for the isolated acetyl derivative 6 (see below), which inferred a molecular formula of C$_{11}$H$_{11}$N$_2$OCl for 4. The presence of an oxygen and an additional unit of unsaturation in 4 as compared to 1 further supported the novelty of this epibatidine congener.

The vapor-phase infrared spectrum from GC-FTIR of 4 was descriptive principally in absorptions that were missing. No C—H stretching vibrations from mono-, di-, or tri-substituted double bonds were observed, though one or more aromatic C—H (3055 cm$^{-1}$) and a chloropyridine with C═C and C═N stretching absorptions (1595 and 1418 cm$^{-1}$) were seen, similar to those in 1. As is common in the vapor-phase IR spectra of amines, no ν$_{NH}$ was observed. However, mass spectrometric data and in-situ derivatization confirmed the presence of a secondary amine. While many bands similar to 1 were observed in 4, the prominent 1110 cm$^{-1}$ band of 1 was missing. Comparison of the IR spectrum of 4 with those of epibatidine, 2-chloropyridine, 2-chloro-6-methylpyridine, and 2-chloro-6-methoxypyridine suggested that the oxygen could be attached to the pyridine 6-position, characterized by a band at 1264 cm$^{-1}$.[5,21] While not compelling evidence by itself, this structural feature was consistent with NMR data shown below, suggesting the oxygen to be adjacent to the pyridine nitrogen at C-7. Interestingly, the GC-FTIR spectrum of 4 displayed an absorption in an unusual region of the spectrum, just below 3000 cm$^{-1}$. The structures of the frog skin alkaloids usually contain five- and six-membered rings, and the absorptions seen in the 2900-3000 cm$^{-1}$ region are usually below 2975 cm$^{-1}$. In the case of 4 the absorption at 2997 cm$^{-1}$ is clearly due to the cyclobutane ring.[22]

NMR analysis of initially isolated 4.DCl[23] indicated an impurity in the sample, but provided useful information. A second HPLC purification gave a cleaner sample but contained a different impurity, a not uncommon experience when working with such tiny samples. Nonetheless, consistencies in the two data sets afforded unambiguous assignments of many structural features.

The $^1$H NMR spectrum of 4.DCl are set forth in Table 1.

TABLE 1

| Position | δ$_H$ (J in Hz) |
| --- | --- |
| 2 | 4.24 (dd 7.5, 7.0) |
| 3α | 2.22 (qd ~11, ~3.4-7.1) |
| 3β | 1.74 (m) |
| 4α | 2.63 (q, 11.5) |
| 4β | 2.38 (t, 11.9) |
| 10 | 7.02 (d, 7.7) |
| 11 | 7.70 (bd, 7.7) |
| 13 | 4.08 (bd, 6.8) |
| 14α | 3.92 (bt, 7.2) |
| 14β | 3.69 (bd, 12.5) |

The $^1$H NMR spectrum of 4.DCl in CD$_3$OD revealed a number of distinctive features. In contrast to 1, only two vicinal aromatic hydrogens were observed. Two doublets at 7.05 and 7.70 ppm, indicated that the chlorine (by analogy with 1) was on one side of the pyridine ring and two other substituents were on the opposite side. The aliphatic portion of the spectrum exhibited two spin systems, one consisting of five spins and another consisting of three spins. There were four resonances in the 3.5-4.5 ppm range. Three of these comprised a single-spin system with the hydrogen assigned as H-13 showing benzylic coupling to H-11 and a methylene (assigned by COSY) adjacent to a heteroatom, which we assigned as the secondary ammonium group. While this is technically a five-spin system because of the benzylic coupling, we consider it here as a three-spin system and a separate two-spin system for simplicity. The remaining midfield signal at 4.24 ppm was part of a five-spin system and was coupled to two consecutive methylenes. This signal was assigned to a cyclobutane system based on COSY data and the observation that the methylene protons were highly non-equivalent, Acetylation of 4 by treatment with excess acetic anhydride and evaporation under nitrogen afforded isolable 6 for analysis by $^1$H NMR spectroscopy. This gave approximately 20 μg of 6, the amount determined by adding a known quantity of $CHCl_3$ to the $CD_3OD$ NMR sample. Acetamide 6 was clearly distinct from N-acetylepibatidine[5] by MS and NMR. HRMS analysis of the isotopic molecular ions at m/z 264 and 266, indicated a molecular formula of $C_{13}H_{13}N_2O_2Cl$, which also established the molecular formula of 4 by difference. The SIMS fragments for 6 at m/z 179, 167 and 80 were mass measured and their formulas determined to be $C_9H_6NO^{35}Cl$, $C_8H_6NO^{35}Cl$, and $C_5H_6N$, respectively. As noted above, these fragments are in the same relative proportions as in 4, thus supporting the assignment of the fragmentations noted for 4.

The $^1$H NMR spectrum of 6 are set forth in Table 2.

TABLE 2

| Position | $\delta_C$ (ppm) $^a$(Major/minor) | $\delta_H$ (J in Hz) Major rotamer | Minor rotamer | 1D irradiation at #H affects: |
|---|---|---|---|---|
| 2 | 65 | 4.70 (dd 7.56, 6.31) | 4.79 (dd 7.56, 6.93) | 2→3α, 3β, 4β; 2'→3α', 3β', 4β' |
| 3α | 20 | 2.45 (ddd, 3.2, 8.0, 11.3) | 2.39 (m) | |
| 3β | | 1.69 (dtd, 6.2, 9.3, 12.0,) | 1.62 (m, 6.5, 8.6) | |
| 4α | 27.5 | 2.53 (m, 0.6, ~2, ~11) | 2.55 (m, 0.4,, 1.5, ~11) | |
| 4β | | 2.37 (m) | 2.35 (m) | |
| 10 | 118.5 | 6.99 (d, 7.69) | 7.01 (d, 7.69) | 10, 10'→11, 11' |
| 11 | 138.3 | 7.69 (dd 7.69, 1.0) | 7.72 (dd 7.66, 1.2) | 11, 11'→10, 10' |
| 13 | 48.4/49.4 | 4.08 (m) | 4.15 (ddd 8.2, 2.8, ~1) | 13 →14α, 14 β; 13'→14α', 14 β'<br>13, 13'→11, 11' (small J removed)<br>13, 13'→3β, 3β' |
| 14α | 53.2/54.6 | 4.08 (m) | 3.96 (dd, 11.6, 3.2) | 14 α' →14 β'; 13'; 14α→ 14 β, 13 |
| 14β | | 4.02 (dd, 7.0, 16.2) | 4.32 (dd, 11.6. 8.3) | 14 β→3 β |
| Ac | 21.6 ($CH_3$) | 2.01 (s) | 2.00 (s) | | tightly coupled, and the system terminated at a quaternary center, as all four signals were at 2.5 ppm or below. The HMQC spectrum of 4 was acquired with the early impure material but gave no conclusive data due to the small sample size and impurities present. By analogy with 1, the chlorine was assigned to C-9 adjacent to the pyridine nitrogen. It was anticipated that the biosynthetic pathway for this unusual function would be analogous to that of 1, suggesting that the position of the chlorine would be conserved in any related metabolites. The remaining two substituents on the pyridine ring were assigned as a furan-ring based on two lines of NMR evidence. First, the previously mentioned benzylic coupling of the broader 7.70 ppm doublet to another doublet resonance at 4.08 ppm was revealed by the COSY spectrum, indicating a carbon-substituent with a benzylic hydrogen at that position. Second, an ether oxygen was required for the structure, as an alcohol was ruled out due to the absence of OH bands in the GC-FTIR spectrum. The assignment of the single exchangeable hydrogen to a secondary amine was made on the basis of in-situ methylation[20] and acetylation in the GC-MS injector. Oxygenation at C-7 was also inferred from comparison of the IR spectrum of 2-chloro-6-methoxypyridine,[21] which bears a significant similarity to that of 4.

A major and a minor rotamer were observed in a 2:1 ratio in the $^1$H NMR spectrum of 6, complicating interpretation, particularly in the aliphatic region. Nonetheless, the spectra provided further evidence for the assignments of some hydrogens, which were aided by 1D decoupling experiments as well as by the 2D TOCSY (with variable mixing times) and HMQC spectra. Notably, H-14α, H-14β and H-2 were shifted downfield in the $^1$H NMR spectrum, due to the acetyl group. The greatest challenge was in the assignment of the cyclobutane resonances, since overlapping signals for the major and minor rotamers produced significant congestion. The signal for H-2 was cleanly related to protons H-3α and H-3β by a TOCSY experiment with a short mixing time (5 ms), while a longer time (30 ms) elaborated H-4α and H-4β. This was also visible for the minor rotamer, but the weak signals made precise assignment difficult. However, selective 1D irradiation of the known multiplets facilitated several assignments as shown in Table 1. Key to the final assignment was the fact that H-3β was observed at unusually high field (1.68/1.60 ppm for major/minor rotamers respectively) for a cyclobutane proton, while H-3α was seen at lower field (2.44/2.37 ppm for major/minor rotamers, respectively). This was consistent with the HMQC spectrum, though the two cross peaks were quite weak, which can be explained on the basis that H-3β projects into the shielding cone above the acetamide n-system[24] and is consistent with molecular models (Chem3D). Protons H-4α (2.35/2.34 ppm) and H-4β (2.47/2.48 ppm) were much closer together, lacking this influence, and were found at chemical shifts more consistent with cyclobutanes.[25] TOCSY spectra were particularly helpful for sorting out the minor rotamer shifts on the basis of cross peaks from the resonance of H-3β, since the rotamers were well-separated. The two aromatic hydrogens were present in a 2:1 ratio of major/minor rotamers with the major rotamer being upheld for both signals. The most downfield proton for H-11 at 7.70 ppm was observed as a doublet of doublets (J=7.7, 1.0 Hz) and long-range coupling to H-13 was observed using 1D decoupling (see Table 1), consistent with 4. An incomplete HMQC spectrum was obtained for 6, with several weaker signals missing, principally those of the minor rotamer. Nonetheless, several useful correlations were seen that aided in structure elucidation. These included the observation that the five-spin system, comprising the remainder of the proton spectrum, arose from protons on three carbons. A portion of this system was present as a complex pattern of overlapping multiplets in the region of ca. 2.3-2.6 ppm and was derived from three protons on two carbons (H-3α and H-4α, H-4β). The remainder of this system was another group of overlapping multiplets at 1.6-1.8 ppm, which was derived from a proton on a single carbon (H-3β, both rotamers).

To aid interpretation of the complex multiplets, the five-spin system of 6 was simulated at 600 MHz (Bruker NMR-SIM) based on isolating the H-4β signal and its couplings and using those with the assignments made for the other four protons H-2 to H-4 of 6. Likewise, the three-spin system of H-13, H-14α, and H-14β of 6 was simulated and coupling constants extracted. The three-spin system comprised two sets of three signals, one ascribed to the major rotamer, the other to the minor rotamer (indicated with the prime (') notation). The minor rotamer was seen clearly with well-separated protons, each appearing as a doublet of doublets, having two vicinal couplings and one geminal coupling. The major rotamer was more complex, yielding a second-order spectrum with H-13 overlapping H-14β and appearing as two triplets with H-14α appearing slightly upfield as a doublet of doublets. The overlap of H-13 and H-14β was shown by the carbon signals at 48.4 and 53.2 ppm for the proton multiplet at 4.07-4.12 ppm. The three-spin simulation with applied $J_{AB}=9$, $J_{AC}=3$ and $J_{BC}=11.8$ Hz was virtually identical to the acquired $^1$HNMR spectrum of 6 at 600 MHz. Selective 1D decoupling independently confirmed these two three-spin systems and allowed coupling constants for the minor rotamer to be determined (see Table 1). In both the minor rotamer and major rotamer, H-13 had a long range coupling (ca. 1 Hz) with the most downfield doublet at 7.73 ppm, which was removed by irradiation at the position of H-13' (4.15 ppm) or H-13 (4.08 ppm), respectively. Molecular modeling (MM2, Chem3D) indicated a dihedral angle between H-13 and H-11 of 117°, making the benzylic C—H bond nearly parallel to the π system, affording efficient coupling.[26]

The rotamer effect on H-4 was minimal. Thus, H-4α and H-4α', each a triplet of doublets, overlapped giving an apparent quartet of doublets. Slightly upfield of this multiplet was a complex multiplet (2.32-2.44 ppm) that 1D decoupling indicated to be from H-3α, 4β, H-4β', and H-3α', with the latter three signals upfield of H-3α. This unfortunate coincidence of three signals made interpretation difficult for this region of the proton spectrum. The most upfield multiplet (1.58-1.75 ppm) of the five-spin system included signals assigned to H-3β and H-3β', with the minor rotamer separated nicely as a multiplet at 1.58-1.62 ppm. Irradiation at H-2 and H-2' removed a small J value from H-4β and H-4β' indicating a long-range coupling between the H-2 and H-4β protons, whereas H-4α and H-4α' in 4 were unaffected. Such long range coupling is not uncommon in rigid systems such as bicyclic terpenes, many with a four-membered ring as part of the structure, where a four-bond coupling is often observed.[27] Also on irradiation at H-2, a medium sized J value was removed from H-3β and an apparent quartet with J ~10 Hz resulted. Irradiation at H-2' had a similar effect on H-3β'. Irradiation at H-2 and H-2' also affected the H-3α and H-3α' signals, respectively, removing a medium J value from each.

The COSY spectrum showed a number of useful cross peaks that were consistent with 1D decouplings, but the resolution was such that unambiguous assignments were limited. A weak cross peak was observed for another long-range coupling between H-14β and H-3β. The spectrum also indicated the multiplet between 2.42-2.45 ppm to be from a single proton (H-3α), showing coupling with H-3β but not with H-3β', and which was cleanly separated at 600 MHz. Other couplings were observed for the five-spin system, but were complicated by the overlap of H-4α with H-4α' and a combined overlap of H-3α', H-4β, and H-4β'. However, 1D decoupling was of significant utility. Irradiation at H-3β again showed the multiplet assigned to H-3α to be a single proton. The reverse decoupling showed the multiplet for H-3β (1.66-1.73 ppm) also to be from a single proton. A large J value was removed in either case judged by the decrease in the width of the multiplets. Irradiation at H-3β removed a large J value from H-2, whereas irradiation at H-3α removed a smaller coupling.

The unusual separation between H-3α and H-3β (Δ=0.75 ppm) in 6 may be suggested as being due to the shielding effect of the acetamide carbonyl. However, a similar but smaller effect for H-3 protons (Δ=0.48 ppm) was seen with the amine 4, which lacks this function. A much smaller effect (Δ=0.16 ppm) was seen with the H-4 protons in both 4 and 6. In both cases, it is the β protons that are shielded, which would suggest an effect from the pyrrolidine nitrogen.

The TOCSY spectrum (30 ms mixing time) showed no coupling between H-3α and H-3β' clearly indicating that each multiplet belonged to separate molecules. Cross peaks between the H-4α/H-4α' overlapping multiplet (2.5-2.6 ppm) and the slightly separated signals for H-3β (1.66-1.71 ppm) and H-3β' (1.64-1.58 ppm) confirmed their respective connectivities. The same TOCSY spectrum showed cross peaks between H-2 and H-3α, H-3β, H-4α and H-4β, all of roughly equal intensity. The three-spin system of the minor rotamer was seen clearly with cross peaks between H-13', H-14α', and H-14β'. The three-spin system of the major rotamer showed only one cross peak as H-13 and H-14α overlapped, but did correlate with H-14β.

Based on these data, the structure for 4 is postulated as shown. The chloropyridine is consistent with NMR and IR data and analogous to 1. Exchange and derivatization data demonstrated the presence of a secondary amine, again consistent with 1. HRMS indicated a single oxygen, for which other data suggested an ether. If the amine is taken to be part of a pyrrolidine system as present in 1, this leaves two rings remaining as no double bond is evident in the proton NMR spectrum. This can be achieved by closure of one ring with the oxygen terminus and pyrrolidine β-carbon, while fusing a cyclobutane with the same pyrrolidine β-carbon and α-carbon producing a condensed tetracycle with a central quaternary center. Molecular modeling of this tetracycle rules out many possible orientations of the oxygen, H-2 and H-13. The structure as shown, having H-13 on the β-face and the oxygen and H-2 on the α-face, most closely approximates the calculated dihedral bond angles (θ) and the H—H couplings observed with 4 and 6 (see below). This is also consistent with two of the C—H orientations (H-2, H-4) seen in 1 as though 4 might be biosynthetically derived from 1 or a common precursor. It appears that migration of the C-1 to C-6 bond in 1 with new bond formation between C-6 and C-3 (C-4 and C-5 in 4) could generate this novel ring system. However, this is only speculative and the role of the oxygen is not clear. The absolute configuration of 4 is not known, but is likely to be that shown. Natural 1 has the (1R,2R,4S) configuration as shown and 4 would be expected to have the R-configuration at C-13 by analogy.

The junctions between the furan, cyclobutane, and pyrrolidine rings were assigned as cis-, since a trans-fusion would be ~18 kcal/mol higher in energy and also incompatible with the observed couplings based on molecular models (Chem3D). The model of 4 indicates a dihedral angle of ~15° between H-13 and H-14β, which would give a vicinal $^3J_{AB}$ of ~7 Hz. Likewise, the dihedral angle between H-13 and H-14α is calculated to be ~104° affording a small $^3J_{AC}$ of ~2 Hz or less. The corresponding trans-fused isomer (with H-13 on the α-face) would have values of 167° and 44° for these respective dihedral angles. This would require larger J values of 10 Hz and 4 Hz respectively, such that neither H-13 nor H-14α could appear as simple doublets as is observed in the $^1$H NMR spectrum of 4. The observed J values of 12.5 Hz (geminal $^2J$, H-14α-H-14β) and 6.8 Hz ($^3J_{AB}$, H-14β-H-13) are therefore consistent with the depicted cis-geometry.

2D-TOCSY and COSY correlation spectra and HMQC data are consistent with the proposed structure although 1D decoupling provided greater insight into the structure because of overlaps that obscured some 2D data of 6. Due to the small sample size, a NOESY required 60 hrs but did show the acetamide methyl correlated with H-2 in the major rotamer and with H-14β' and H-14α' in the minor rotamer. Another key non-scalar cross peak observed at 600 MHz was that of H-4β with H-13, again supporting the relative stereochemistry of both ring junctions as cis.

Biological Investigation of Phantasmidine. Semi-preparative HPLC-bioassay analysis was conducted as described previously on the alkaloid fraction of *E. anthonyi* in several cell lines, including TE-671 (neuromuscular),[16] SH-SY5Y (ganglionic α3*, α3β4*, α7),[15] and several transfected cell lines expressing nicotinic receptor subunit combinations of α2-4 and β2/β4.[12,13,17]

The separated fractions afforded several activities at various times depending on the cell line examined, although most of the agonist activity was limited to the early (5-20 min) range. Epibatidine (1)[5] was easily identified by APCI-MS at 13.25 min and was active in all cell lines to varying degrees, with the greatest activity being in cells transfected with α3 and β4 subunits. This is consistent with the known pharmacological profile of epibatidine.[8,19,13] Epiquinamide (2)[9] was identified at 6 min, although its activity was later found to be an artifact due to a cross-contamination from 1.[10] The relative activity of 2 across the various cell lines was also consistent with that of 1. A third major area of activity was found at 15 min and corresponded to an APCI-MS peak at 15.2 minutes having m/z 222/224. Initially it was thought to be a methyl-epibatidine and indeed, N-methylepibatidine (3) was identified by APCI-MS at 13 min, being confirmed by comparison with previously synthesized material.[7] Compound 3 was responsible for the leading edge of the epibatidine activity in the bioassay profile. However, the third activity was clearly not a methylated epibatidine as HRMS indicated the presence of an oxygen and an additional unit of unsaturation. Consequently, the alkaloid, named as phantasmidine, was isolated and its structure (4) determined as described above.

Based on the previous observation that epiquinamide was incorrectly assigned activity due to contamination of the fractions with the very potent epibatidine,[10] it initially was of concern that the activity of 4 might be due to similar contamination. This was allayed by the careful observation of the relative activity of 4 as compared to 1 based on the height and area of the activity peaks. Eluting at 13.25 min, 1 consistently displayed the greatest activity in the sample regardless of cell line examined. The activity initially ascribed to 2 at 6 min was of consistent relative size in each cell line, supporting cross-contamination by 1 as the likely explanation for its activity. However, 4, which eluted at 15.20 min, showed higher relative activities in cell lines expressing β44 nicotinic subunits (KXα3β4R2,[12] KXα4β4R1,[13] IMR-32,[14] SH-SY5Y[15]) and less activity in neuromuscular (TE-671)[16] and β2-containing (KXα4β2R2,[13] K-177[17]) cells. This suggested that 4 has an altered selectivity relative to 1 and may, like 1, find use as a pharmacological probe.

The N—N distance in 4 is calculated to be approximately 5.1 Å (MM2, Chem3D), consistent with the currently proposed nicotinic pharmacophore of epibatidine.[45-47] It is representative of an epibatidine conformation in which the chloropyridine ring is essentially coplanar with C-5 and C-13, which comprise the proximal bridge of the azabicycle (see Figure 15). Subtle, but perhaps significant differences in the vector orientation of potential H-bonding sites at the two nitrogens can be observed, which may contribute to the observed selectivity.[46]

The following examples further illustrate the invention but, of course, should not be construed as in any way limiting its scope.

General Experimental Procedures. Reagents and solvents used were of ACS reagent or HPLC grades and were used as received. NMR analysis was performed on Varian Inova 500 MHz and Bruker Avance II 600 MHz spectrometers. Chemical shifts (δ) are reported in ppm relative to TMS and coupling constants (J) are reported in Hz. GC-MS was conducted using a Finnigan GCQ in EI and CI (NH$_3$ or ND$_3$) modes using an RTX-5MS column (25 m×0.25 mm i.d.) and a temperature program of 100° C. held for 1 min followed by a ramp to 280° C. at 10° C./min then held at 280° C. for 10 min. GC-FTIR spectra were acquired using a Hewlett Packard 5890 GC (same column except 0.32 mm i.d., same temperature program) interfaced with a narrow band 5965B infrared detector. HPLC-MS was performed using an Agilent 1100 binary HPLC system interfaced with a Finnigan LCQ ion trap mass spectrometer. Molecular modeling was performed using Chem3D Pro (v. 8.0, Cambridge Scientific Computing, Cambridge Mass.). NMR spectral simulations were performed using NMRSIM (Bruker, v. 4.3).

Example 1

This example describes initial processing of material obtained from animals.

Collection of specimens of *Epipedobates anthonyi* (formerly *E. tricolor*), preparation of extracts and HPLC separation were essentially as described previously.[9] Briefly, the alkaloid fraction from the methanolic extract of 183 skins (net 6 mL at 13 g skin/mL) was analyzed by HPLC-UV-MS using a Phenomenex Aqua 125 Å C$_{18}$ column (4.6×250 mm) and a gradient of H$_2$O/CH$_3$CN, with each component containing 0.1% HOAc, from 90 to 50% H$_2$O over 40 min and held 10 min. For biological analysis, otherwise identical runs were conducted with only UV detection and collection of the eluate into 96-well plates covering the interval of 4 to 64 min using an Isco Foxy 200 fraction collector. The collected fractions were acidified with HCl to suppress volatility, evaporated under nitrogen flow, sealed with PARAFILM™ and kept at −20° C. until use.

Example 2

This example describes a bioassay of chromatography fractions obtained from the material described in Example 1.

Collected analytical scale fractions in 96-well plates were reconstituted in situ with 300 μL Hanks balanced salt solution containing 20 mM HEPES at pH 7.4 (HBSS/HEPES) and were used as such. Cell lines expressing various nicotinic receptors were maintained in culture and used for functional fluorescence assays including SH-SY5Y, IMR-32, TE-671, KXα3β4R2, KXα4β4R1, and KXα4β2R2, as previously described.[9,11] Briefly, cells were plated onto 96-well poly-D-lysine-coated plates in Dulbecco's modified minimum essential media supplemented with 10% fetal bovine serum (supplemented with Geneticin G418 for KXα3β4R2, KXα4β4R1, and KXα4β2R2 cells) and grown to near confluence. The media was aspirated and the cells were gently washed with 2×100 μL HBSS/HEPES (pH 7.4). A solution of Molecular Devices no-wash membrane potential dye (30 μL) was added and the cells incubated in the dark at room temperature for 1 h. Plates were read on a FLEXSTATION™ (Molecular Devices) robotic plate reader at an excitation wavelength of 530 nm, emission wavelength of 565 nm, with a cutoff filter at 550 nm. Basal fluorescence was measured for 15 s and 30 μL of reconstituted $E.$ $anthonyi$ fraction in HBSS/HEPES were added. Response was measured for 105 s and 304 of 300 μM nicotine were added. The nicotine response was measured for 40 s and 30 μL of 160 mM KCl were added. Maximal fluorescence was measured for 40 s. Average basal fluorescence was subtracted and response was taken as the peak fluorescence for each addition divided by the maximal KCl fluorescence. Responses for each fraction were plotted as a function of time and compared to the UV and total ion chromatograms to identify active components. Preparative-scale isolation was then conducted and structures of active components were elucidated.

Example 3

This example describes the isolation of phantasmidine (4).

Preparative isolation was conducted as previously described.[9] Briefly, 5 mL of the extract was concentrated under a nitrogen flow to ~0.3 mL and separated by HPLC in a similar fashion with collection in deep-well polypropylene plates using a Phenomenex Aqua 125 Å $C_{18}$ column (10×250 mm) at 2.0 mL/min with collection of fractions at 0.25 mL/min over six injections. Fractions of this eluate, found to contain 4, were collected and analyzed by LC-APCI-MS, GC-MS in EI and CI ($NH_3$, $ND_3$) modes, GC-FTIR and microprobe NMR (500 MHz). The initially collected fractions were found to be insufficiently pure for unambiguous NMR analysis and were re-chromatographed as above. This provided material which was slightly impure, but allowed unambiguous identification of the NMR signals belonging to 4.

Phantasmidine (4).

$E.$ $anthonyi$ alkaloid extract LC peak, $R_t$ 15.20 min, GC peak, $R_t$ 14.66 min: UV (LC $CH_3CN/H_2O$, 0.05% HOAc) $\lambda_{max}$ 260 nm; IR (vapor) $v_{max}$ 2997, 2960, 2846, 1595, 1418, 1309, 1264, 1217, 1111, 1079, 1041, 931, 810 cm$^{-1}$; $^1$H NMR (500 MHz, $CD_3OD$) δ 7.70 (1H, d, J=7.7, <1 Hz, H-11), 7.02 (1H, d, J=7.7 Hz, H-10), 4.24 (1H, dd, J=7.5, 7.1 Hz, H-2), 4.08 (1H, br.d, J=6.8 Hz, H-13), 3.92 (1H, br.t, J=~7.2 Hz, H-14α), 3.69 (1H, br.d, J=12.5 Hz, H-14(3)), 2.63 (1H, q, J=11.5 Hz, H-4α), 2.38 (1H, t, J=11.9 Hz, H-4(3)), 2.22 (1H, app qd, J=3.4, 11.5 Hz, H-3α), 1.74 (1H, m, H-3β); EIMS m/z 224 (7), 223 (3), 222 (20), 221 (7), 209 (2), 207 (6), 196 (3), 194 (8), 193 (4), 181 (2), 179 (4), 169 (34), 167 (100), 131 (5), 130 (4), 80 (89), 56 (46); EIMS (with trace $ND_3$, major peaks only) m/z 170 (30), 168 (91) (one exchange), 130 (7, no exchange), 81 (100), 57 (67); EI-MS/MS on m/z 167 m/z 152 (3), 149 (167-$H_2O$, 17), 138 (167-CH=O, 100), 131 (167-$H^{35}Cl$, 24), 113 (167-$H_2O$—$H^{35}Cl$, 59), 104 (167-63, 52); CIMS ($NH_3$) m/z 223 (100), 225 (32); CI-MS/MS (on m/z 223) 223 (M+H, 32), 206 (M+H—$NH_3$, 44), 195 (M+H—$C_2H_4$, 100), 194 (46), 188 (36), 187 (43), 169 (11), 160 (20), 159 (38), 143 (15), 132 (20); CI-MS/MS (on m/z 225) 225 (M+H, <5), 224 (40), 223 (22), 208 (M+H—$NH_3$, 22), 207 (19), 197 (M+H—$C_2H_4$, 100), 196 (66), 190 (32) 187 (52), 169 (22), 161 (25), 160 (34), 159 (25), 143 (14), 132 (15); HRFABMS m/z 223.0650 (calcd for $C_{11}H_{12}N_2O^{35}Cl$, 223.0638).

Example 4

This example describes the preparation and characterization of N-methylphantasmidine (5).

N-Methylphantasmidine (5).

Co-injection of 4 with formalin and formic acid[19] afforded in-situ methylation to give 5: GC-MS showed: $R_t$ 14.28 min; EIMS m/z 238 (3), 236 (11), 223 (2), 221 (5), 210 (2), 208 (7), 195 (3), 193 (10), 181 (4), 179 (11), 168 (5), 166 (12), 94 (100), 70 (34).

Example 5

This example describes the preparation and characterization of N-acetylphantasmidine (6).

N-Acetylphantasmidine (6).

Co-injection of 4 with acetic anhydride afforded in-situ acetylation to give 6. GC-MS showed a single peak, $R_t$ 17.82 min; IR (vapor) $v_{max}$ 2959, 1693, 1598, 1418, 1260, 1233, 1086, 935, 764 cm$^{-1}$; NMR data are given in Table 1; EIMS m/z 266 (75), 264 (25), 251 (6), 249 (21), 224 (14), 222 (43), 209 (8), 207 (30), 205 (23), 196 (11), 194 (36), 181 (47), 179 (63), 169 (33), 167 (100), 165 (50), 140 (5), 138 (9), 131 (4), 130 (19), 104 (9), 102 (17), 84 (20), 80 (89), 75 (10), 56 (42); HREIMS m/z 264.0673 (calcd for $C_{13}H_{13}N_2O_2^{35}Cl$, 264.0666), 266.0642 (calcd for $C_{13}H_{13}N_2O_2^{37}Cl$, 266.0636), 179.0142 (calcd for $C_9H_6NO^{35}Cl$, 179.0138), 167.0126 (calcd for $C_8H_6NO^{35}Cl$ 167.0132), 80.0500 (calcd for $C_5H_6N$, 80.0500). To a partially evaporated methanolic residue of 4 was added excess acetic anhydride and the mixture was allowed to stand overnight, followed by evaporation of excess anhydride under nitrogen flow to afford 6.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES AND NOTES (1) Daly, J. W.; Spande, T. F.; Garraffo, H. M. *J. Nat. Prod.* 2005, 68, 1556-1575.
(2) Daly, J. W. *J. Med. Chem.* 2003, 46, 447-452.
(3) Daly, J. W. *Cell. Mol. Neurobiol.* 2005, 25, 513-552.
(4) Jensen, A. A.; Frolund, B.; Liljefors, T.; Krogsgaard-Larsen, P. *J. Med. Chem.* 2005, 48, 4705-4745.
(5) Spande, T. F.; Garraffo, H. M.; Edwards, M. W.; Yeh, H. J. C.; Pannell, L.; Daly, J. W. *J. Am. Chem. Soc.* 1992, 114, 3475-3478.
(6) Badio, B. Garraffo, H. M., Spande, T. F.; Daly, J. W *Med. Chem. Res.* 1994, 4, 440-449.
(7) Badio, B.; Shi, D.; Garraffo, H. M.; Daly, J. W. *Drug. Dev. Res.* 1995, 36, 46-59.
(8) Dukat, M.; Glennon, R. A. *Cell. Mol. Neurobiol.* 2003, 23, 365-378.
(9) Fitch, R. W.; Garraffo, H. M.; Spande, T. F.; Yeh, H. J. C.; Daly, J. W. *J. Nat. Prod.* 2003, 66, 1345-1350.
(10) Fitch, R. W.; Sturgeon, G. D.; Patel, S. R.; Spande, T. F.; Garraffo, H. M.; Daly, J. W.; Blaauw, R. H. *J. Nat. Prod.* 2009, 72, 243-247.
(11) Fitch, R. W.; Daly, J. W.; Kellar, K. J.; Xiao, Y. *Proc. Natl. Acad. Sci. USA* 2003, 100, 4909-4914.
(12) Xiao, Y.; Meyer, E. L.; Thompson, J. M.; Surin, A.; Wroblewski, J.; Kellar, K. J. *Mol. Pharmacol.* 1996, 54, 322-333.
(13) Xiao, Y.; Kellar, K. J. *J. Pharmacol. Exp. Ther.* 2004, 310, 98-107.
(14) Lukas, R. J. *J. Pharmacol. Exp. Ther.* 1986, 265, 294-302.
(15) Lukas, R.; Norman, S.; Lucero, L. *Mol. Cell. Neurosci.* 1993, 4, 1-12.
(16) Lukas, R. J. *J. Neurochem.* 1986 46, 1936-1941.
(17) Gopalakrishnan, M.; Monteggia; L. M., Anderson, D. J.; Molinari, E. J.; Piattoni-Kaplan, M.; Donnelly-Roberts, D.; Arneric, S. P.; Sullivan, J. P. *J. Pharmacol. Exp. Ther.* 1996, 276, 289-297.
(18) The postulated MS fragmentations were considered after the structure was proposed with help from the NMR spectra.
(19) Brewer, A. R. E. In *Name Reactions for Functional Group Transformations*; Li, J. J.; Corey, E. J., Eds., Wiley and Sons: Hoboken, N.J., 2007; Ch. 2, pp 86-92.
(20) Daly, J. W.; Ware, N.; Saporito, R. A.; Spande, T. F.; Garraffo, H. M. *J. Nat. Prod.* 2009, 72, 1110-1114.
(21) Pouchert, C. J. *Aldrich Library of FT-IR Spectra: Vapor Phase*, Vol. 3; Aldrich Chemical Co.: Milwaukee, Wis., 1989; p 1531A.
(22) Nyquist, R. A. *Interpreting Infrared, Raman, and Nuclear Magnetic Resonance Spectra*; Academic Press: San Diego, 2001; Vol. 1, pp 35, 48-49.
(23) Following HPLC, the fractions were acidified with HCl to suppress volatility, thus the spectra of 4 are of the corresponding DCl salt on exchange with $CD_3OD$.
(24) Ring current effects are a common explanation for such effects (e.g., Pople, J. A.; Schneider, W. G.; Bernstein, H. J. *High-Resolution Nuclear Magnetic Resonance*; McGraw-Hill: New York, 1959). However, this has recently been challenged on the basis of computational data. See: Wannere, C. S.; Schleyer, P. V. R. *Org. Lett.* 2003, 5, 605-608.
(25) Silverstein, R. M.; Webster, F. X.; Kiemle, D. *Spectrometric Identification of Organic Compounds*, $7^{th}$ Ed. Wiley and Sons: New York, 2005; Ch. 3, pp 192-193.
(26) Lambert, J. B.; Mazzola, E. *Nuclear Magnetic Resonance Spectroscopy: An Introduction to Principles, Applications and Experimental Methods*, Pearson Prentice Hall: Upper Saddle River, N.J., 2004; Ch. 4, pp. 112-115.
(27) Jackman, L. M.; Sternhell, S. *Applications of Nuclear Magnetic Resonance Spectroscopy in Organic Chemistry*, $2^{nd}$ Ed. Pergamon Press: New York, 1969; Vol. 5, Table 4-4-6, p 336.
(28) Parker, M. J.; Beck, A.; Luetje, C. W. *Mol. Pharmacol.*, 1998, 54, 1132-1139.
(29) Decker, M. W.; Reuter, L. E.; Bitner, R. S. *Curr. Top. Med. Chem.* 2004, 4, 369-384.
(30) Sacco, K. A.; Bannon, K. L.; George, T. P. *J. Psychopharmacol.* 2004, 18, 457-474.
(31) Etter, J. F.; Lukas, R. J.; Benowitz, N. L.; West, R.; Dresler, C. M. *Drug. Alcohol Depend.* 2008, 92, 3-8.
(32) Jorenby, D. E.; Hays, j. T.; Rigotti, N. A.; Azoulay, S.; Watsky, E. J.; Williams, K. E.; Billing, C. B.; Gong, J.; Reeves, K. R. *J. Am. Med. Assoc.* 2006, 296, 56-63.
(33) Avalos, M.; Parker, M. J.; Maddox, F. N.; Carroll, F. I.; Luetje, C. W. *J. Pharmacol. Exp. Ther.* 2002, 302, 1246-1252.
(34) Sharples, C. G. V.; Kaiser, S.; Soliakov, L.; Marks, M. J.; Collins, A. C.; Washburn, M. S.; Wright, E.; Spencer, J. A.; Gallagher, T.; Whiteaker, P.; Wonnacott, S. *J. Neurosci.* 2000, 20, 2783-2791.
(35) Kedmi, M.; Beaudet, A. L.; Orr-Urtreger, A. *Physiol. Genomics* 2004, 17, 221-229.
(36) Salas, R.; Pieri, F.; De Biasi, M. *J. Neurosci.* 2004, 24, 10035-10039.
(37) Carroll, F, I.; Hu X.; Navarro, H. N.; Deschamps, J.; Abdrakhmanova, G. R.; Damaj, M. I.; Martin, B. R. *J. Med. Chem.* 2006, 49, 3244-3250.
(38) Kanne, D. B.; Tomizawa, M.; Durkin, K. A.; Casida, *J. E. Bioorg. Med. Chem. Lett.* 2005, 15, 877-881.
(39) Pabreza, L. A.; Dhawan, S.; Kellar, K. *J. Mol. Pharmacol.* 1991, 39, 9-12.

(40) Astles, P. C.; Baker, S. R.; Boot, J. R.; Broad, L. M.; Dell, C. P.; Keenan, M. *Curr. Drug Targets: CNS Neurol. Disorders* 2002, 1, 337-348.
(41) Baker, S. R.; Cases, M.; Keenan, M.; Lewis, R. A.; Tan, P. *Tetrahedron Lett.* 2003, 44, 2995-2999.
(42) Broad, L. M.; Felthouse, C.; Zwart, R.; McPhie, G. I.; Pearson, K. H.; Craig, P. J.; Wallace, L.; Broadmore, R. J.; Boot, J. R.; Keenan, M.; Baker, S. R.; Sher, E. *Eur. J. Pharmacol.* 2002, 452, 137-144.
(43) Baker, S. R.; Boot, J.; Brunays, M.; Dobson, D.; Green, R.; Hayhurst, L.; Keenan, M.; Wallace, L. *Bioorg. Med. Chem. Lett.* 2005, 15, 4727-4730.
(44) Dorff, P.; Gordon, J.; Heys, J. R.; Keith, R. A.; McCarthy, D. J.; Phillips, E.; Smith, M. A. World Patent, WO2005030778, 2005.
(45) Glennon, R. A.; Herndon, J. L.; Dukat, M. *Med. Chem. Res.* 1994, 4, 461-473.
(46) Glennon, R. A.; Dukat, M. *Bioorg. Med. Chem. Lett.* 2004, 14, 1841-1844.
(47) White, R.; Malpass, J. R.; Handa, S.; Baker, S. R.; Broad, L. M.; Folly, L.; Mogg, A. *Bioorg. Med. Chem. Lett.* 2006, 5493-5497.
(48) Kellar, K. J.; Xiao, Y. In *Handbook of Contemporary Neuropharmacology*; Sibley, D. R.; Hanin, I.; Khar, M., Skolnick, P., Eds., Wiley and Sons: New York, 2007; Ch. 4, pp 107-146.
(49) Bunnelle, W. H.; Dart, M. J.; Schrimpf, M. R. *Curr. Top. Med. Chem.* 2004, 4, 299-334. Table 1. NMR Data for 4 and 6 (500 MHz, $CD_3OD$).

The invention claimed is:

1. A compound of the formula:

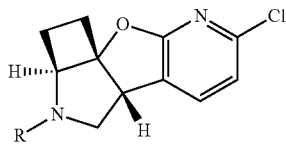

wherein R is $CH_3$ or $CH_3CO$, or a pharmaceutically acceptable salt thereof.

2. The compound of claim 1, wherein R is $CH_3$, or a pharmaceutically acceptable salt thereof.

3. The compound of claim 1, wherein R is $CH_3CO$, or a pharmaceutically acceptable salt thereof.

4. A pharmaceutical composition comprising a pharmaceutically acceptable carrier and a compound of salt of claim 1.

5. A pharmaceutical composition comprising a pharmaceutically acceptable carrier and a compound of salt of claim 2.

6. A pharmaceutical composition comprising a pharmaceutically acceptable carrier and a compound of salt of claim 3.

* * * * *